(12) United States Patent
Westbrook et al.

(10) Patent No.: US 8,430,102 B2
(45) Date of Patent: Apr. 30, 2013

(54) ORAL DEVICE FOR RADIOTHERAPY

(75) Inventors: Tony Westbrook, Lafayette, LA (US); Sheila Wartelle, Carencro, LA (US); Grover Bass, Sunset, LA (US)

(73) Assignee: OncoLogics, Inc., Lafayette, LA (US)

( * ) Notice: Subject to any disclaimer, the term of this patent is extended or adjusted under 35 U.S.C. 154(b) by 271 days.

(21) Appl. No.: 12/750,903

(22) Filed: Mar. 31, 2010

(65) Prior Publication Data

US 2011/0240040 A1    Oct. 6, 2011

(51) Int. Cl.
*A61C 5/14* (2006.01)

(52) U.S. Cl.
USPC .......................................................... 128/860

(58) Field of Classification Search .................. 128/857, 128/859, 860, 861, 862, 200.26; 433/6, 93, 433/139, 140
See application file for complete search history.

(56) References Cited

U.S. PATENT DOCUMENTS

| 3,132,647 | A | 5/1964 | Giuseppe |
| 4,676,240 | A * | 6/1987 | Gardy ............................ 128/848 |
| 5,533,523 | A | 7/1996 | Bass et al. |
| 5,666,973 | A | 9/1997 | Walter |
| 6,060,083 | A | 5/2000 | Dorr et al. |
| 6,244,866 | B1 | 6/2001 | Campbell |
| 6,629,971 | B2 | 10/2003 | McDaniel |
| 6,655,960 | B2 | 12/2003 | Fischer |
| 6,675,804 | B1 | 1/2004 | Pivovarov |
| 6,676,655 | B2 | 1/2004 | McDaniel |
| 6,716,029 | B2 | 4/2004 | Fischer et al. |
| 6,887,260 | B1 | 5/2005 | McDaniel |
| 6,936,044 | B2 | 8/2005 | McDaniel |
| 6,976,491 | B2 * | 12/2005 | D'Agosto ..................... 128/859 |
| 7,004,933 | B2 | 2/2006 | McDaniel |
| 7,107,997 | B1 | 9/2006 | Moses et al. |
| 7,137,393 | B2 | 11/2006 | Pivovarov |
| 7,201,765 | B2 | 4/2007 | McDaniel |
| 7,494,503 | B2 | 2/2009 | McDaniel |
| 7,520,281 | B1 * | 4/2009 | Nahabedian ................. 128/848 |
| 7,607,439 | B2 | 10/2009 | Li |
| 8,028,705 | B2 | 10/2011 | Li |
| 8,251,069 | B2 | 8/2012 | Burdumy et al. |
| 8,261,748 | B1 | 9/2012 | Goldberg |
| 2002/0123746 | A1 | 9/2002 | McDaniel |
| 2002/0144685 | A1 | 10/2002 | Ivanovich et al. |
| 2003/0004499 | A1 | 1/2003 | McDaniel |
| 2003/0129154 | A1 | 7/2003 | McDaniel |
| 2004/0267236 | A1 | 12/2004 | Sun et al. |

(Continued)

OTHER PUBLICATIONS

International Search Report dated May 11, 2011 in related PCT Application No. PCT/US11/23567 filed Feb. 3, 2011, 2 pages.

(Continued)

*Primary Examiner* — Patricia Bianco
*Assistant Examiner* — Raymond E Harris
(74) *Attorney, Agent, or Firm* — Eric L. Sophir; SNR Denton US LLP

(57) ABSTRACT

A oral device for use in radiotherapy is disclosed. The device is a two piece adjustable mouthpiece for use during radiotherapy of the head and neck. The device provides immobilization of the tongue for accurate reproducible administration of radiation therapy. The device fits within the oral cavity of a patient and is maintained in position by a bite-member that fits over the maxillary teeth of the patient. The adjustable feature of the device allows the device to fit the mouth to accommodate differences in mouth cavities and bite profile.

7 Claims, 4 Drawing Sheets

U.S. PATENT DOCUMENTS

| | | |
|---|---|---|
| 2005/0149150 A1 | 7/2005 | McDaniel |
| 2005/0261750 A1 | 11/2005 | McDaniel |
| 2005/0283211 A1 | 12/2005 | McDaniel |
| 2006/0129209 A1 | 6/2006 | McDaniel |
| 2006/0184214 A1 | 8/2006 | McDaniel |
| 2006/0212025 A1 | 9/2006 | McDaniel |
| 2006/0217690 A1 | 9/2006 | Bastin et al. |
| 2006/0265030 A1 | 11/2006 | McDaniel |
| 2007/0191822 A1 | 8/2007 | McDaniel |
| 2007/0289600 A1 | 12/2007 | Li |
| 2008/0097278 A1 | 4/2008 | Cole et al. |
| 2009/0131499 A1 | 5/2009 | Castro et al. |
| 2009/0196903 A1 | 8/2009 | Kliman |
| 2009/0311347 A1 | 12/2009 | Oronsky et al. |
| 2010/0132720 A1 | 6/2010 | Razmovski |
| 2010/0256550 A1 | 10/2010 | McDaniel |

OTHER PUBLICATIONS

International Search Report dated Apr. 20, 2011 in related PCT Application No. PCT/US11/23572 filed Feb. 3, 2011, 2 pages.

International Search Report dated May 10, 2011 in related PCT Application No. PCT/US11/23575 filed Feb. 3, 2011, 2 pages.

Lacouture et al., Evolving Strategies for the Management of Hand-Foot Skin Reaction Associated with the Multitargeted Kinase Inhibitors Sorafenib and Sunitinib, The Oncologist, 2008, pp. 1001-1011, vol. 13.

Perez-Soler et al., HER1/EFGR Inhibitor-Associated Rash: Future Directions for Management and Investigation Outcomes from the HER1/EGFR Inhibitor Rash Management Forum, The Oncologist, 2005, pp. 345-356, vol. 10.

\* cited by examiner

ORAL DEVICE FOR RADIOTHERAPY

FIELD OF THE INVENTION

The present invention is directed to a device for use during administration of radiation therapy to patients with head and neck cancers. Specifically, the present invention is directed to a mouthpiece to be inserted into the mouth during radiation therapy of the neck or head.

BACKGROUND OF THE INVENTION

Head and neck cancers are a major cause of morbidity and mortality worldwide, and comprise a group of related cancers originating from the aerodigestive tract, and may involve the oral cavity, the lips, pharynx, larynx, nasal cavity, and paranasal sinuses. Cancer of the esophagus is also included among the head and neck cancers. The incidence of the specific types of head and neck cancer vary greatly throughout the world. For example, although rare in other regions, there is a high incidence of nasopharyngeal carcinoma, a human squamous cell cancer, in Southeast Asia and North Africa. The majority of head and neck cancers are squamous cell carcinomas.

Treatment of head and neck cancer may involve surgery to remove the cancer or radiotherapy and/or chemotherapy to destroy the cancer cells. Radiotherapy or radiation therapy remains the primary treatment for head and neck cancer. Radiotherapy uses high-energy x-rays given as external beam radiotherapy or internal beam radiotherapy to kill cancer cells or to stop them from growing further. Although radiotherapy can affect both cancer cells as well as normal cells, but normal cells are better able to resist or recover from the effects. The area of treatment for head and neck cancer varies, and may involve, for example, the back of the throat, as well as the lymph glands in the neck. The treatment is planned carefully to ensure that the rays are targeted precisely onto the cancerous area, and to do as little harm as possible to the surrounding healthy tissues and minimize side effects such as dry mouth (xerostomia) and inflamed mucous membranes (mucositis). Other side effects from poorly directed radiation include dental decay (caries) and death of bone tissue (osteoradionecrosis).

If the patient can be accurately positioned for repeat sessions of radiotherapy, then side effects may be minimized. It is therefore necessary to perform each session of radiotherapy with the patient in an identical position. This can be problematic for the radiotherapy to tumors in the head and neck areas because the patient's lower jaw and tongue are inclined to change position even when the head is held securely.

In order to enable the affected area to be held in the same precise position for treatment, a mask or shell is molded for a patient that is used in combination with a mouthpiece to immobilize the patient and prevent unnecessary exposure of normal tissue to radiation. The mouthpiece is used to depress the patient's tongue onto the floor of the patient's mouth. This helps minimize the movement of the patient's tongue and jaw during the radiation procedure. Traditional mouthpieces are made of contoured wax or are molded to fit the patient's mouth. Among the disadvantages of wax mouthpieces, they must be molded individually for each patient, and may change shape depending on the storage temperature or the temperature inside the patient's mouth. The present mouthpiece is designed to be used quickly and with ease, and to be adjustable depending on the shape of the patient's and the patient's individual bite profile.

Therefore, it is an object of the present invention to provide a device for reducing movement or immobilizing the patient's tongue and to open the patient's jaw during treatment.

It is also an object of the present invention to provide a device that suppresses the tongue with reduced or minimal contact with the tongue.

It is also an object of the present invention to provide a device that permits radiation to pass through the device to reduce effects on surrounding tissue.

It is also an object of the present invention to provide a device for head and neck radiotherapy that is adjustable to accommodate a patient's bite profile and mouth size.

SUMMARY OF THE INVENTION

The present invention is directed to a device for use during administration of head and neck radiotherapy. The device is a mouthpiece that inserts into the mouth for immobilizing the patient's tongue during radiation treatment. Preferably, a hollow base reduces scattering of radiation as it passes through the device to the affected tissues.

In one aspect, the device includes a base and an adjustable bite member. The base includes a platform and a multi-level block on the superior surface of the platform. The multi-level block is preferably hollow and may be accessible through a hole in the platform. In one embodiment, the platform has ridges on the inferior surface, typically in a half circle shape. The multi-level block member typically has at least two levels of different elevation on the superior surface, and will usually include three or more different levels to accommodate the oral cavity of a range of patients. The bite member is reversibly secured to the base. For example, each level of the base member may include a hole adapted to receive a pin of a bite-member that is to be attached to the base.

The base is preferably cast from a non-toxic, biocompatible, and optionally biodegradable material that is injection moldable and retains its shape when exposed to radiation.

The above and other objects, features, and advantages of the present invention will become apparent from the following description read in conjunction with the accompanying drawings.

DETAILED DESCRIPTION OF THE INVENTION

The present invention relates to a device for use during administration of radiation therapy during treatment of cancers of the head and neck. The device comprises an adjustable mouthpiece to be inserted into the oral cavity prior to radiation therapy of the neck or head to immobilize the tongue and open the jaw to permit irradiation of the affected tissue. The device is preferably adjustable for different mouth cavities and bite profiles. The device comprises a substantially hollow base member to minimize scattering of radiation that would affect healthy surrounding tissues. The small size of the device also permits air to move freely when positioned inside the mouth, making it easy for an individual to breathe when the device is inserted into the mouth.

Figure 3:
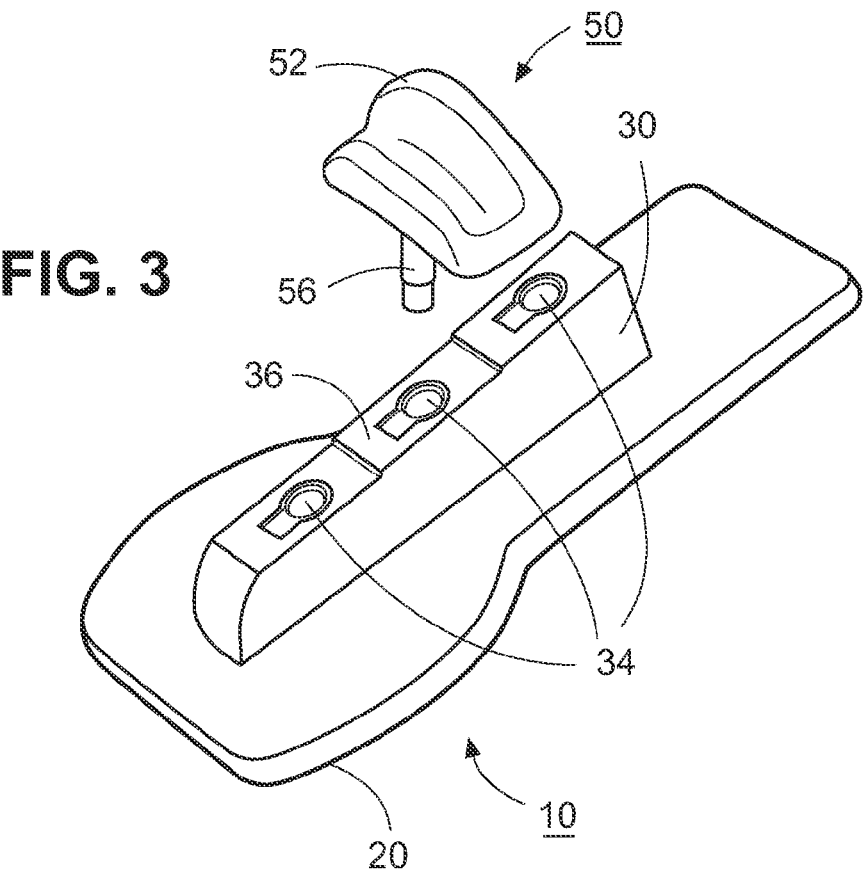
FIG. 3 provides an overhead-view schematic showing one embodiment of the devices described herein.

With reference to the drawings, the device illustrated in FIG. 3 includes a base member 10 and a separable adjustable bite-member 50. Base member 10 includes a platform 20 which is positioned over the tongue and which depresses the tongue during use. As shown in FIG. 3, the platform is preferably substantially planar in shape and wider in the lateral dimension at one end (the proximal end) than the other (the distal end). Base member 10 also includes a generally block-shaped portion 30 which rises above the platform and which has differential heights, increasing from the proximal end of the platform (i.e., the end of the platform inserted into the mouth) to the distal end. Block-shaped member 30 has at least one means for reversibly coupling to the adjustable bite-member 50. The means for reversibly coupling to the adjustable bite-member 50 to the base member 10 may be, for example, a pin and hole coupling, a screw, a snap, adhesive tape, Velcro, or the like. As shown in FIG. 3, in one embodiment of the invention, the bite-member 50 includes a pin or rod 56 and block-shaped member 30 has one or more holes 34 to receive the pin or rod 56.

The block-shaped member 30 may have two or more terraced levels 36, each level containing a hole 34 for receiving the pin or rod 56. Any number of steps may be included, for example, one, two, three, four, five or six steps are contemplated. The steps may ascend or descend from the proximal to distal end. The adjustable bite member 50 may be positioned on any level of the multi-level block member 30 of the base member 10 by inserting the pin or rod 56 into a desired hole 34 based on the size of the patient's oral cavity. The platform member 20 and multi-level block member 30 may be molded together so that the base 10 is a single continuous unit. In another embodiment, the platform 20 and multi-level block 30 are fabricated separately and affixed together after they are created to form the base member 10.

Figure 1:
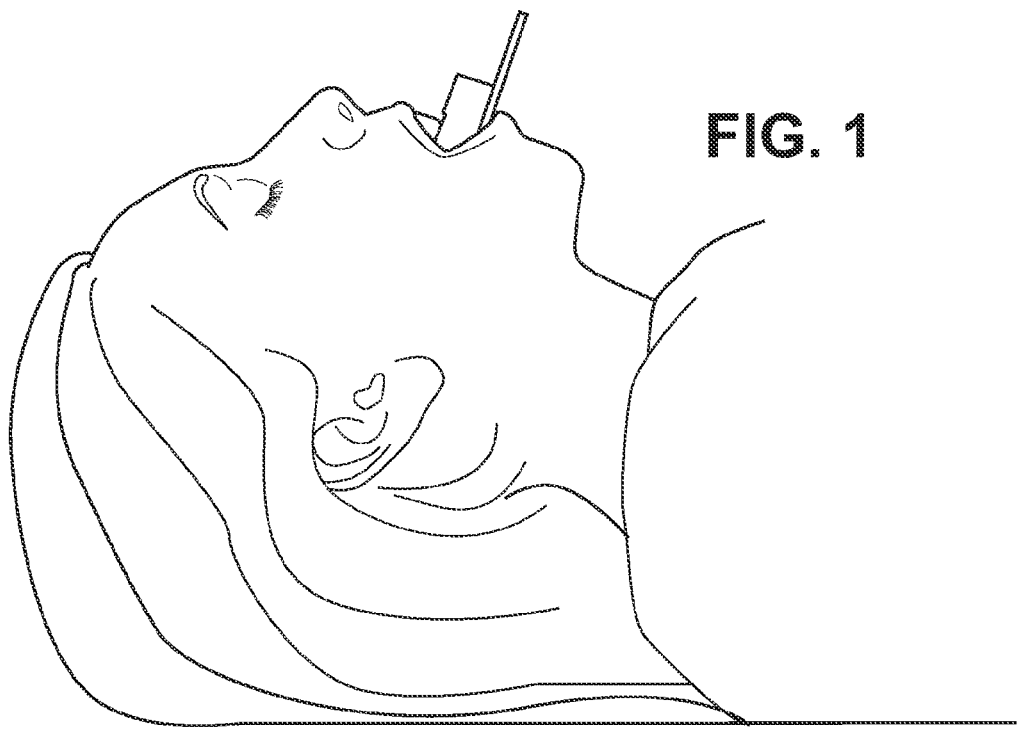
FIG. 1 provides a side-view schematic showing the placement in the oral cavity of one embodiment of the devices described herein.
Figure 2:
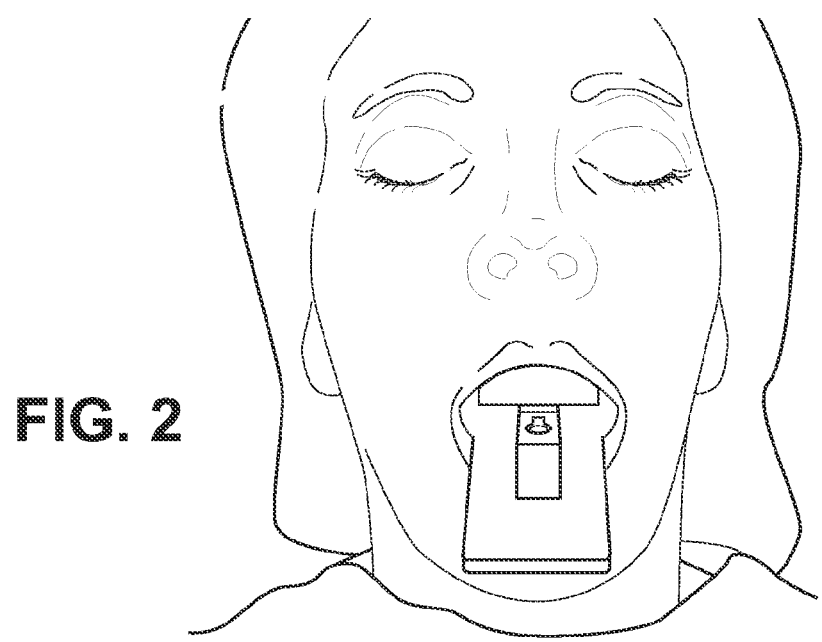
FIG. 2 provides a front-view schematic showing the placement in the oral cavity of one embodiment of the devices described herein.

The platform member 20 has a superior (top) and inferior (bottom) surface. The platform has proximal end, which is positioned in the oral cavity of a patient, and a distal end which extent outward from the mouth as depicted in FIGS. 1 and 2. In the embodiment shown in FIG. 3, the platform 20 is rounded at the proximal end to generally conform to the contours of the oral cavity.

Preferably the device is positioned to minimize contact with tissue inside the oral cavity. Contact between the device and tissues inside the mouth may cause increased scattering of radiation and minimize the efficacy and targeting of the radiation treatment. To reduce or minimize contact between the inferior surface of the base and the patient's tongue, there may be a plurality of raised structures 26 (shown in FIG. 4) that function to suppress or immobilize the patient's tongue while minimizing contact between the tongue tissue, and base of the device. In some embodiments, the raised structures may be round angular, square, hexagonal, octagonal, or any similar shape that protrudes from the inferior surface of the base. In other embodiments, the raised structures may be, for example, a series of ridges that span the underside of the base laterally or longitudinally or at any angle to lateral or longitudinal orientation. In a specific embodiment shown in FIGS. 4 and 6-8, the raised structures 26 are generally circular-shaped bumps on the inferior surface of the base. In some embodiments, the raised structures extend from about 2 to about 20 mm (preferably from about from 5-15 mm or about 7-10 mm) from the inferior surface of the base.

Figure 6:
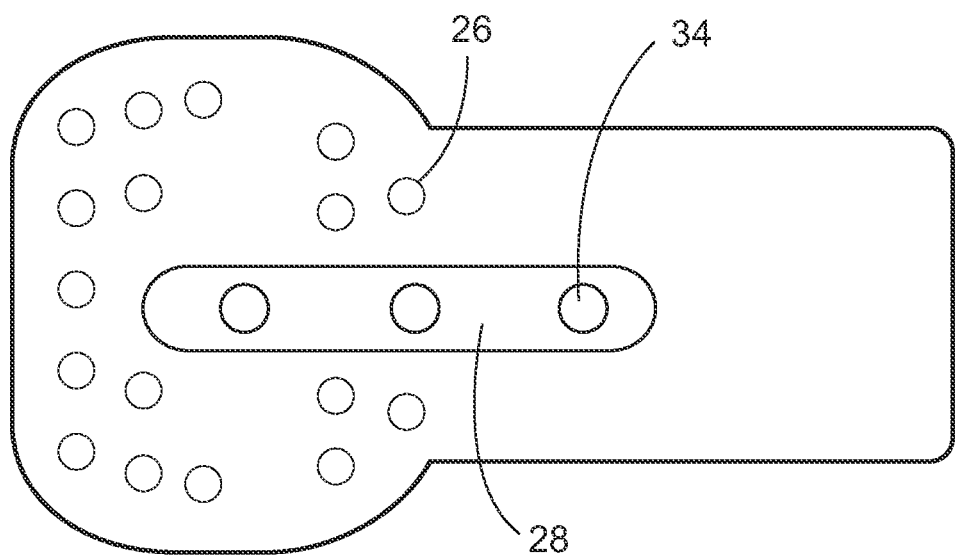
FIG. 6 provides an inferior view of the device showing the opening to the hollow cavity inside one embodiment of the devices described herein.
Figure 7:
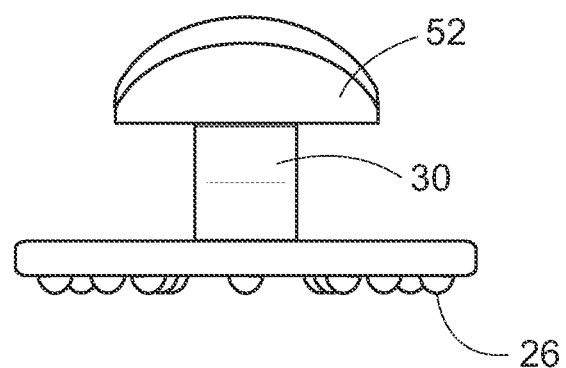
FIG. 7 provides an anterior-view schematic of one embodiment of the devices described herein.
Figure 8:
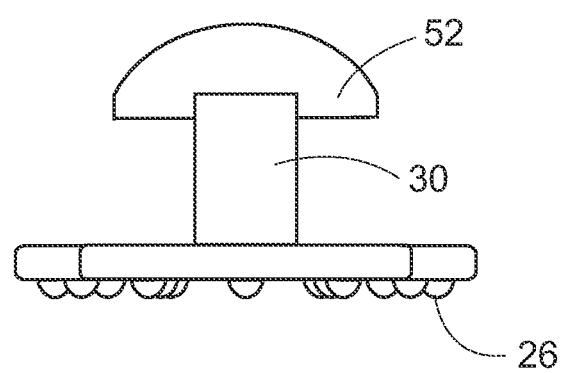
FIG. 8 provides an posterior-view schematic of one embodiment of the devices described herein.

In a preferred embodiment, the multi-level block 30 is substantially hollow such that holes 34 open into a cavity within the block. The cavity is illustrated in FIG. 6 and includes an opening 28 on the inferior surface of platform 20. In the embodiment shown in FIG. 6, the one or more holes 34 are visible through opening 28 when base 10 is viewed from its inferior surface.

Figure 4:
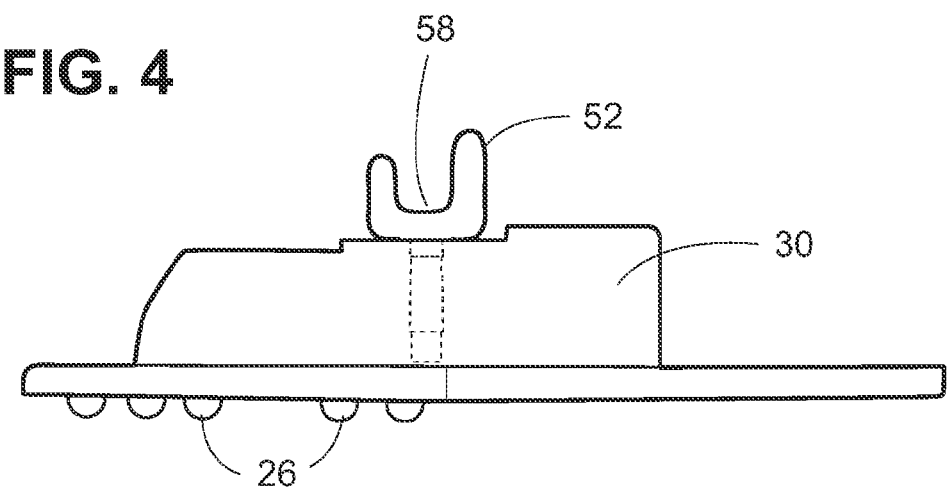
FIG. 4 provides a side-view schematic of one embodiment of the devices described herein with the adjustable bite-member inserted in the central position.
Figure 5:
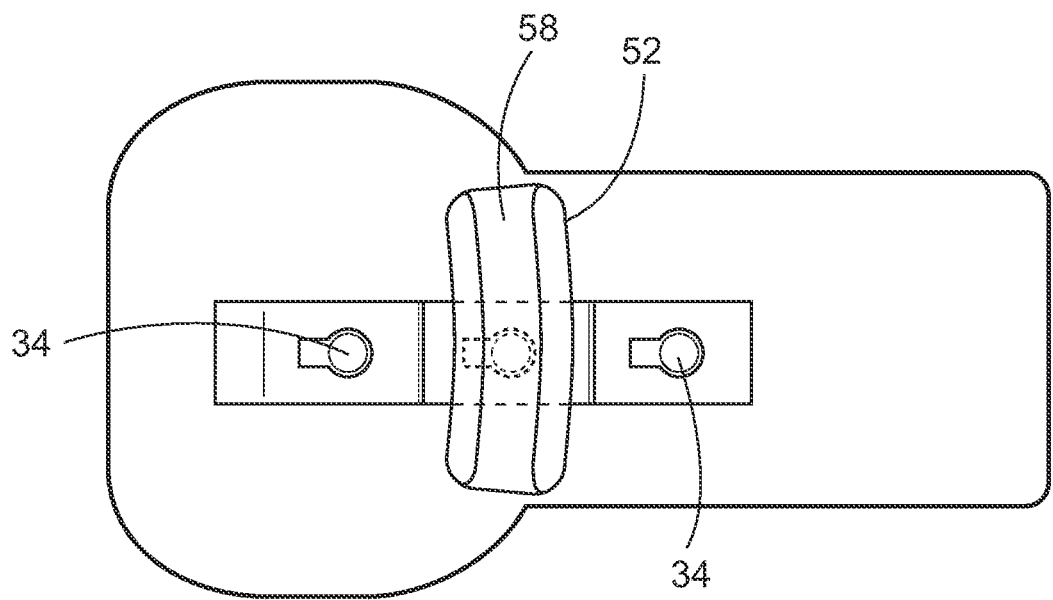
FIG. 5 provides a superior view of one embodiment of the devices described herein.

Bite-member 50 is separable from the base 10 and is reversible attached to base 10 by inserting pin 56 into hole 34 as illustrated in FIG. 4. Bite-member 50 includes a tooth/gum tray 52, having a groove 58 which accommodates the front teeth of the upper jaw in use. In one embodiment, pin 56 is a key and locking tapered barrel pin. The locking pin may be incorporated on the post to prevent rotation of the tooth/gum tray 52. Alternatively, the pin 56 may be sized appropriately to fit firmly into the holes 34 of the multi-level block 30. In one embodiment, a mirrored receiver cavity is formed in each step of the multi-level block 30 to assist in locking the tooth/gum tray 52 securely to the base. The tooth/gum tray 52 is fitted with a groove 58 to receive a maxillary row of teeth of a patient on the superior surface of the tooth/gum member. This tooth/gum tray 52 may be curved so as to generally fit an average maxillary row of teeth from a human, or else may be made of a moldable material that may be pre-molded to substantially conform to the maxillary row of teeth of a patient. The bite member 50 may be slightly curved to accommodate the curvature of the teeth as shown in FIG. 5. The position of the bite-member 50 is adjustable when joined to the base 10 depending on the size of the mouth of the patient. The multi-level positioning of the bite member accommodates the device for different sizes of mouth cavities and bite profiles.

In one embodiment, the tooth/gum tray 50 is pre-molded before radiation treatment to substantially conform to the patient's maxillary teeth. This permits a customized device that permits reproducible radiotherapy in multiple sessions. In this embodiment, the tooth/gum tray 50 may be made from a radiolucent material such as Aquaplast RT Thermoplastic which includes 2-Oxepanone polymer with 1,4-butanediol. The tooth/gum tray 50 may be immersed in water at 70° Celsius to soften the material and then inserted into the patient's mouth to obtain an impression of the patient's maxillary teeth. The radiolucent material hardens and the tooth/gum tray 50 is removed from the patient's mouth. This embodiment allows for a customized device that is partially reusable. The base of the device may be sterilized and reused and the bite-member 10 may be discarded after radiation treatment is complete. In one embodiment, the bite member and/or base are disposable. Effective sterilization methods include but are not limited to autoclave, UV irradiation, and gas sterilization.

Materials

The mouthpiece described herein is preferably made from a soft plastic material to allow for bite compression. Preferably, the materials are inert, non-toxic or biocompatible materials that will not react with human tissues when placed into the mouth cavity or subjected to radiation of the radiotherapy treatment. In one embodiment, the materials are FDA-approved for use in human subjects.

In a preferred embodiment, the material for the bite member 50 is a 40-50 Durometer A Scale injection molded material. Such materials include, but are not limited to, rubber such as, but not limited to silicone, soft vulcanized rubber, natural nitrile and the like. Other materials include elastomeric materials such as GR-S, GR-1, neoprene, thiokol, or the like. In a preferred embodiment, the material for the base is a flexible, high impact styrene vacuum-formed material (HIPS).

Other materials for use in molding the present device include radiolucent materials which allow the passage of X-rays or other radiation. Radiolucent materials include, but are not limited to plastic, thermosets, such as phenolics and epoxies; thermoplastics—including a wide range of materials such as polyolefins, polyesters, nylons, polycarbonates, polyurethanes, and polyketones. The material may also include medical radiolucent composites such as thermoplastic resins with carbon-fiber reinforcement.

Dimensions

The dimensions of the base 10 and bite-member 50 are such that they accommodate being fit into a human mouth cavity. In specific embodiments, the base 10 will measure about 8-12 cm in length, about 9-11 cm in length, or about 10.5 cm in length. Usually, the base will protrude from the mouth of an individual when positioned therein. Alternatively, the entire device may fit substantially in the mouth of an individual during use. In specific embodiments, the base will measure about 4-7 cm, or about 5.0 cm in width at the proximal end and will measure about 2-5 cm or about 3.8 cm at the distal end. The height of the platform 20 of the base 10 is typically between 3 and 8 mm, preferably about 5 mm. The width of the multi-level block 30 is not particularly important and will typically range from about 0.8 cm and 1.8 cm. The height of the platform 20 will typically be between about 1.0 and 2.5 cm.

Use of the Device

The device described herein can be used during radiotherapy of the head and neck where the device is positioned inside the mouth so that the patient's upper row of teeth rests in the groove 58 of the superior surface of the tooth/gum tray 52. Placement of one embodiment of the device in the oral cavity is shown in FIG. 1 and FIG. 2. The bite-member 50 is positioned in a hole 34 of the multi-level block member to permit a secure fit of the device in the patient's mouth. The bite member may be adjusted anteroposterior relative to the base member to fit optimally for an individual's mouth size and bite profile. The device is positioned to depress the tongue in order to minimize or reduce tongue movement, or immobilize the tongue. Placement of the device also opens the jaw, and provides reproducible positioning of the jaw and tongue for specific exposure to radiation during radiotherapy. Further, the hollow base minimizes scattering of radiation to healthy surrounding tissues.

While the invention has been described with reference to certain preferred embodiments, numerous changes, alterations and modifications to the described embodiments are possible without departing from the spirit and scope of invention as defined in the appended claims, and equivalents thereof.

The invention claimed is:

1. An adjustable mouthpiece for use in radiation therapy comprising: a base member and a bite-member, said base member and bite-member being suitably sized and configured for positioning in the oral cavity of a human patient, such that the base member depresses the patient's tongue when positioned in the oral cavity, and the bite-member accommodates the front teeth of the patient's upper jaw, wherein said base member includes a substantially hollow cavity to reduce scattering of radiation and said bite-member is adjustable in height in an anteroposterior direction relative to the base member, wherein the base member comprises a platform having an end configured to be placed into the patient's mouth and a block-shaped member rising above said platform on one face thereof, said block-shaped member comprising two or more holes for reversibly engaging a pin coupled to the bite-member, wherein each of the two or more holes provides a different height of the bite-member relative to the base member.

2. The adjustable mouthpiece of claim 1 comprising a plurality of ridges or bumps on the face of said platform opposite said block-shaped member.

3. The adjustable mouthpiece of claim 1 wherein the mouthpiece comprises a radiolucent material.

4. A method of immobilizing a patient's jaw and tongue during radiation therapy comprising inserting the adjustable mouthpiece according to claim 1 into the oral cavity of said patient.

5. A method of immobilizing a patient's jaw and tongue during radiation therapy comprising inserting the adjustable mouthpiece according to claim 1 into the oral cavity of said patient.

6. A method of immobilizing a patient's jaw and tongue during radiation therapy comprising inserting the adjustable mouthpiece according to claim 1 into the oral cavity of said patient.

7. A method of immobilizing a patient's jaw and tongue during radiation therapy comprising inserting the adjustable mouthpiece according to claim 1 into the oral cavity of said patient.

* * * * *